(12) United States Patent
Ogata et al.

(10) Patent No.: US 6,582,667 B1
(45) Date of Patent: Jun. 24, 2003

(54) SHELL-AND-TUBE REACTOR

(75) Inventors: Yousuke Ogata, Himeji (JP); Takehiro Takashima, Himeji (JP); Osamu Dodo, Hyogo-ken (JP); Hidefumi Haramaki, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/394,087

(22) Filed: Sep. 13, 1999

(30) Foreign Application Priority Data

Sep. 18, 1998 (JP) .......................................... 10-265245

(51) Int. Cl.$^7$ ................ B01J 8/06; F28F 9/22; F28D 7/00; F28D 21/00
(52) U.S. Cl. .................. 422/201; 422/196; 422/197; 422/205; 165/108; 165/112; 165/161
(58) Field of Search ................ 422/201, 173, 422/189, 191, 192, 193, 196, 197, 198, 200, 205, 211; 165/108, 112, 158, 159, 161

(56) References Cited

U.S. PATENT DOCUMENTS

| | | | |
|---|---|---|---|
| 2,638,407 A | | 5/1953 | Steeves ...................... 422/197 |
| 2,852,564 A | | 9/1958 | Warner et al. ............... 568/471 |
| 4,024,329 A | * | 5/1977 | Lauer et al. .................. 526/61 |
| 4,119,670 A | * | 10/1978 | Tsuchiya ..................... 564/477 |
| 4,127,389 A | * | 11/1978 | Hackemesser et al. ....... 422/201 |
| 4,135,889 A | * | 1/1979 | Mori ............................. 48/73 |
| 5,048,601 A | | 9/1991 | Yamaguchi et al. ......... 165/140 |
| 5,821,390 A | | 10/1998 | Ruppel et al. .............. 568/470 |

FOREIGN PATENT DOCUMENTS

| | | |
|---|---|---|
| DE | 973 726 | 5/1960 |
| GB | 2 089 674 | 6/1982 |
| JP | 48-85485 | 11/1973 |
| JP | 61138527 | 6/1986 |
| JP | 62121644 | 6/1987 |
| JP | 8217405 | 8/1996 |

OTHER PUBLICATIONS

Patent Abstracts of Japan, vol. 011, No. 349 (C–456), Nov. 14, 1987, JP 62 121644, Jun. 2, 1987.
[Instance 2.1] Direct Propylene Oxidizing Reaction Apparatus [Fixed–layer type gas–solid catalyst reaction apparatus], pps. 61–66, Feb. 25, 1984, (With English Translation).

* cited by examiner

*Primary Examiner*—Jerry D. Johnson
*Assistant Examiner*—Alexa A. Doroshenk
(74) *Attorney, Agent, or Firm*—Oblon, Spivak, McClelland, Maier & Neustadt, P.C.

(57) ABSTRACT

A shell-and-tube reactor has a plurality of reaction tubes incorporated therein, a circulation path for the heating medium formed outside the reaction tubes, a heating medium introducing section provided on the upper part of the shell in the reactor and a heating medium discharge section provided on the lower part of the shell in the reactor, a back pressure applying means for the heating medium is further provided in the heating medium discharge section.

13 Claims, 4 Drawing Sheets

SHELL-AND-TUBE REACTOR

BACKGROUND OF THE INVENTION

1. Field of the Invention

The present invention relates to a catalytic vapor-phase oxidation method and a shell-and-tube reactor and, more particularly, to a catalytic vapor-phase oxidation method capable of effectively removing reaction heat, that is generated when a raw material gas passes through reaction tubes and reacts, thereby suppressing the occurrence of hot spot (excessively high temperature region localized in catalyst layer), during catalytic vapor-phase oxidation reaction wherein a reaction accompanied by a very large amount of heat generation is carried out at a high temperature in a fixed bed shell-and-tube reactor, and a shell-and-tube reactor preferably used in the method.

2. Description of the Prior Art

In a shell-and-tube reactor, a space outside (shell side) of reaction tubes is filled with a heating medium to circulate the heating medium therein, and a reaction raw material is supplied into the reaction tubes to react therein, while the heat generated during the reaction is removed by means of the heating medium, thereby maintaining predetermined reacting conditions.

FIG. 1 shows a typical example of the shell-and-tube reactor of the prior art. In FIG. 1, numeral 1 denotes a reactor, 2 denotes a raw material gas inlet, 3 denotes a catalyst, 4 denotes a reaction tube, 5 denotes a product gas discharge port, 6a denotes an upper tube supporting plate, 6b denotes a lower tube supporting plate, 7a, 7b, 7c denote baffle plates, 8 denotes a heating medium inlet nozzle, and 9 denotes a heating medium outlet nozzle. The raw material gas comprising a mixture of a reaction raw material and air is supplied through the raw material gas inlet 2 into the reactor 1, allowed to flow in the reaction tube 4 that is filled with the catalyst 3 and, after being oxidized in the reaction tube to turn into a reaction product, is discharged through the product gas discharge port 5. The catalyst 3 for the catalytic vapor-phase oxidation reaction may consist of either a single kind of material or two or more kinds of material, and is packed in the plurality of reaction tubes 4 that are fixed onto the upper and lower tube supporting plates 6a, 6b.

The heating medium that fills and circulates in the space of the reactor on the shell side for removing the reaction heat is introduced through the heating medium inlet nozzle 8 formed on the lower part of the shell of the reactor, and is discharged to the outside of the system through the heating medium outlet nozzle 9 after removing the reaction heat while allowing to flow in a direction to counter the flow of the raw reaction material gas in the axial direction. The baffle plates 7a, 7b, 7c are installed in the shell of the reactor so that the direction of the heating medium flow is changed and the temperature difference across a horizontal plane is reduced, thereby making it possible to keep the heating medium flowing uniformly in the reactor shell and keep the temperature in all reaction tubes at similar levels. The raw material gas may be, for example, propylene, isobutylene, benzene, xylene, naphthalene, acrolein and methacrolein, that produce acrolein and methacrolein, maleic anhydride, phthalic anhydride, acrylic acid and methacrylic acid, etc. through catalytic vapor-phase oxidation.

In most of the shell-and-tube reactors of the prior art, the heating medium is circulated to flow in the axial direction of the reaction tube to counter the flow of the reaction raw material that is charged through the top of the reactor and flows through the reaction tubes, as shown in FIG. 1. As a consequence, the heating medium charged from the outside of the reactor to the lower part of the shell of the reactor, gradually heated to high temperatures through heat exchange while moving up in the reactor, and heat exchanging capacity decreases near the raw material gas inlet of the reaction tubes (top of the reaction tube) where the reaction heat is generated at the highest rate.

Particularly the catalytic vapor-phase oxidation is a process carried out at a high temperature with a very large amount of heat generation, and is often accompanied by excessively high temperature regions localized (hot spot). Therefore it has been required to take such measures as keeping the concentration of the reaction material at a low level or reducing the reaction temperature, in the catalytic vapor-phase oxidation using the shell-and-tube reactor of the prior art, thus making it difficult to maintain the reacting conditions steady. There has also been such a problem that the occurrence of the hot spot may decrease the catalytic activity thus resulting in lower productivity. Thus it is very important to suppress the occurrence of hot spot for a shell-and-tube reactor where catalytic vapor-phase oxidation is carried out in an industrial scale.

Japanese Unexamined Patent Publication (Kokai) No. 48-85485 discloses a method of suppressing the occurrence of the hot spot in reactor tubes by reducing the reactor tube diameter and diluting the catalyst with an inert material. However, this method employs such reacting conditions that do not cause hot spot, and requires it to increase the number of reactor tubes and use a much larger reactor in order to ensure a certain level of production volume.

Japanese Unexamined Patent Publication (Kokai) No. 8-92147 discloses a method of carrying out catalytic vapor-phase oxidation by allowing the heating medium to flow upward from the lower part of the shell in the reactor while supplying a reaction gas at a lower portion of the reactor and discharging it through the top of the reactor. This method makes it possible to prevent hot spot from occurring near the raw material gas inlet. However, since the raw material gas inlet is located at a lower portion, when two or more types of catalyst are used and life expectancy is different between the catalyst used in the first stage and that of the second and subsequent stages, all the catalysts must be changed even in such a case as it is desired to change only the catalyst located at a lower position near the raw material gas inlet. Also in such a case as the catalyst is in the process of partial deterioration due to adsorption blocking of carbide or the like near the raw material gas inlet, differential pressure in the reactor increases that makes it difficult to maintain steady reacting conditions unless the part of catalyst deteriorated due to adsorption blocking of carbides or the like near the raw material gas inlet is removed and replaced. Moreover, since the deteriorated catalyst affects the entire catalyst and leads to shorter active life of the catalyst, it is necessary to periodically remove the catalyst located near the raw material gas inlet. In this case, much labor is required to replace the catalyst with the construction of allowing the raw material gas to flow from below upward.

Therefore, it is common to allow the raw material gas to flow from the top downward when carrying out such a reaction that requires it to periodically remove the catalyst, located near the raw material gas inlet, that is subject to adsorption blocking of carbides or the like, and the method disclosed in Japanese Unexamined Patent Publication (Kokai) No. 8-92147 is generally not in use.

SUMMARY OF THE INVENTION

Under the circumstances described above, the present invention has been accomplished, and an object thereof is to provide a catalytic vapor-phase oxidation method that makes it easy to replace only the catalyst located near the raw material gas inlet and to suppress the occurrence of hot spot with a construction of allowing the raw material gas to flow from the top of the reactor downward, and a shell-and-tube reactor that can be preferably used in the method.

The catalytic vapor-phase oxidation method according to the present invention that solved the problems described above is a catalytic vapor-phase oxidation method wherein, using a shell-and-tube reactor comprising a plurality of reaction tubes incorporated between an upper tube supporting plate and a lower tube supporting plate of the reactor, a heating medium that absorbs reaction heat is circulated while surrounding the reaction tubes, while the reaction tubes are filled with a catalyst and a raw material gas is supplied, thereby to proceed the reaction, said method comprising: allowing the raw material gas to flow downward from the top of the reaction tubes and also allowing the heating medium to flow downward from the upper part of the shell in the reactor, as well as discharging gas, that is introduced along with the heating medium and stores below the upper tube supporting plate of the reactor, to the outside of the reactor. In the method described above, it is desirable to take out the heating medium taken out of the reactor at the bottom thereof, force it to move upward and charge it into the reactor through the upper part of the shell in the reactor, while replacing a predetermined portion of the heating medium taken out of the reactor with a cold heating medium newly supplied from the outside.

The shell-and-tube reactor according to the present invention that solved the problems described above is a shell-and-tube reactor having a plurality of reaction tubes incorporated therein, a circulation path for the heating medium formed outside the reaction tubes, a heating medium introducing section provided on the upper part of the shell in the reactor and a heating medium discharge section provided on the lower part of the shell in the reactor, said reactor further comprising a back pressure applying means for the heating medium in the heating medium discharge section. Further in the shell-and-tube reactor having a plurality of reaction tubes incorporated between an upper tube supporting plate and a lower tube supporting plate of the reactor thereof having a circulation path for the heating medium formed outside the reaction tubes, a pipe may also be installed right below the upper tube supporting plate for discharging a gas, that is introduced together with the heating medium and stores therein, to the outside of the reactor.

DESCRIPTION OF THE PREFERRED EMBODIMENTS

According to the present invention, the catalytic vapor-phase oxidation is performed in a fixed-bed type shell-and-tube reactor by supplying and allowing a raw material gas to flow downward from the top of the reactor and supplying a heating medium from the top of the reactor shell, too, thereby causing the raw material gas and the heating medium to flow in parallel in the axial direction of the reaction tubes. Thus reaction heat is absorbed by the heating medium of a low temperature in the upper zone of the reaction tubes where the exothermal effect is highest, during the catalytic vapor-phase oxidation wherein the raw material gas is supplied to the reactor in down flow, thereby achieving smooth temperature distribution in the axial direction in the reaction tubes and maintaining proper reacting conditions in the reaction tubes while preventing hot spot from occurring.

In case the heating medium is allowed to flow downward from the top of the reactor, however, a space without the heating medium tends to be generated below the upper tube supporting plate in the upper zone of the reactor, causing gas build-up(gas stagnation) in the reactor shell thus producing a localized portion where heat cannot be removed sufficiently, when the gas is introduced into the reactor shell, thus giving rise to a possibility of localized excessive temperature rise that makes it difficult to maintain stable reacting conditions.

This problem can be solved by forcing up the heating medium, that has collected the reaction heat and has been taken out of the reactor at the bottom thereof, and then discharging it to the outside of the reactor, thereby keeping the reactor shell always filled with the heating medium. Alternatively, a pipe may be installed below the upper tube supporting plate for discharging the gas.

Figure 1:
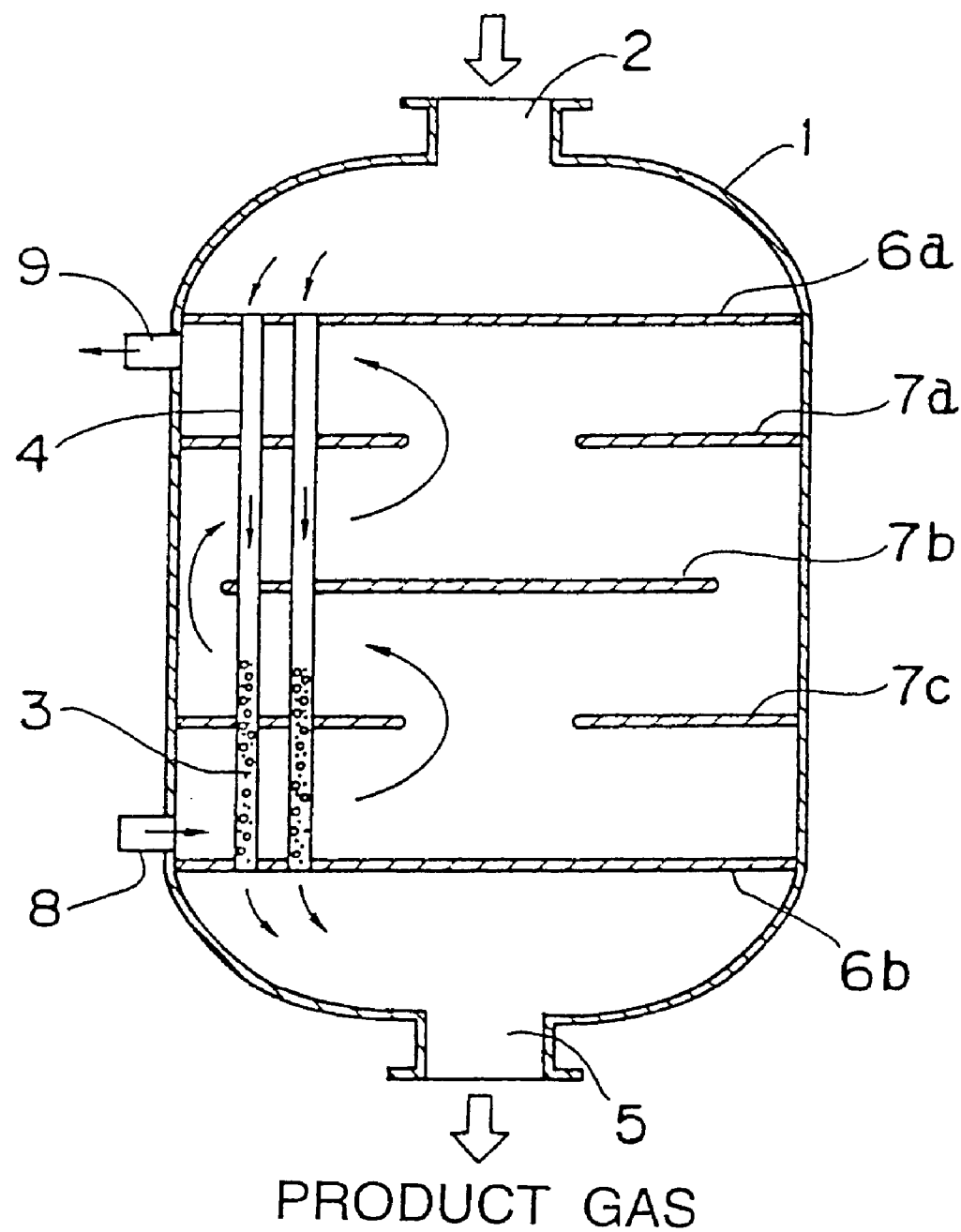
FIG. 1 is a schematic explanatory view showing a shell-and-tube reactor of the prior art.
Figure 2:
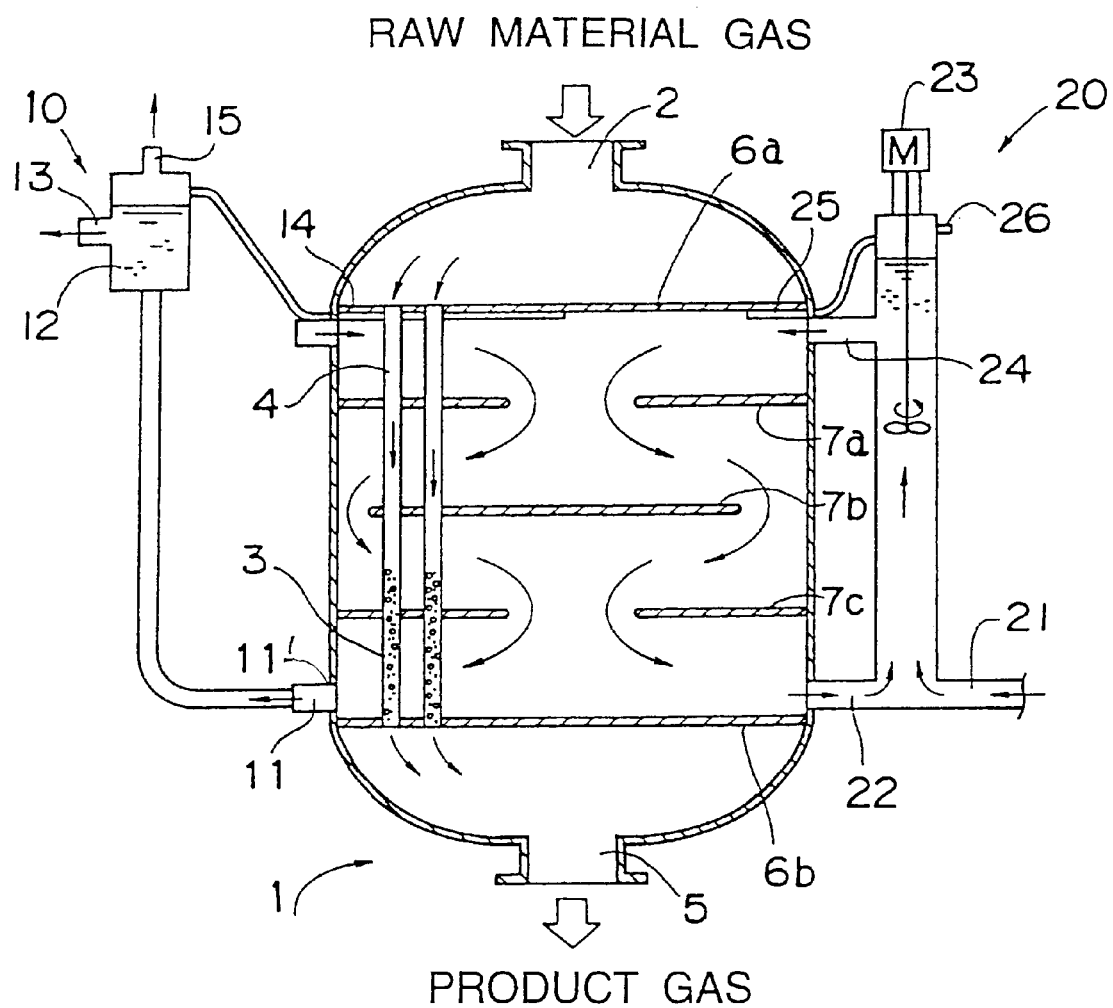
FIG. 2 is a schematic explanatory view showing a shell-and-tube reactor according to the present invention.

FIG. 2 schematically shows a typical example of the shell-and-tube reactor according to the present invention. Numeral 1 denotes a reactor, 2 denotes a raw material gas inlet, 3 denotes a catalyst, 4 denotes a reaction tube, 5 denotes a product gas discharge port, 6a denotes an upper tube supporting plate, 6b denotes a lower tube supporting plate, 7a, 7b, 7c denote baffle plates, 11 denotes a heating medium discharge port, 12 denotes a heating medium discharge pot, 13 denotes a nozzle, 21 denotes a cold heating medium inlet pipe, 22 denotes a heating medium discharge pipe, 23 denotes a pump and 24 denotes a heating medium inlet pipe.

The raw material gas comprising a mixture of a reaction raw material and air is supplied through the raw material gas inlet 2 into the reactor 1, allowed to flow in the reaction tubes 4 that are filled with the catalyst 3 and, after being oxidized in the reaction tubes to turn into a reaction product, is discharged through the product gas discharge port 5.

A predetermined portion of the heating medium after collecting the reaction heat is taken out through the heating medium discharge port 11 of a back pressure applier 10, located at a lower position of the reactor, and the extracted heated medium is forced to move up to the heating medium discharge pot 12 of the back pressure applier 10, disposed above the upper tube supporting plate 6a of the reactor and is then discharged through the nozzle 13 to the outside.

Cold heating medium of the same quantity as the heating medium discharged through the heating medium discharge pot to the outside is supplied through the heating medium inlet pipe 21. Inside of the reactor shell is thus kept full of the heating medium. The cold heating medium and the heating medium recovered from the heating medium discharge pipe 22 are mixed while being pumped up by the pump 23 such as an axial pump or a volute pump, the mixture being supplied through the heating medium inlet pipe 24 into the reactor. The quantity of the cold heating medium to be supplied may be controlled according to an increase in the reaction temperature due to deterioration of the catalyst with time.

Supply of the heating medium to the reactor shell and discharge therefrom are preferably carried out evenly in the circumferential direction of the reactor via ring-shaped pipes that are disposed on the circumference of the reactor in the upper and lower portions and communicate with each other intermittently over the entire circumference.

Discharging the heating medium from the reactor to the outside may not necessarily be done after forcing the heating medium to move up to the upper tube supporting plate of the reactor, as long as the reactor shell can be kept full of the heating medium. The reactor shell may be kept full of the heating medium by providing back pressure via the back pressure applier 10, which has a back pressure applying means at the heating medium discharge port 11 in the lower portion of the reactor shell or before and after thereof thereby applying a sufficient back pressure for the heating medium flowing in the reaction tubes. The back pressure applying means may be, for example, a resistive orifice 11', a valve or a heat exchanger.

Further, in case the heating medium is caused to flow from the top downward in the shell of reactor, gas introduced accompanying the heating medium being supplied tends to build up in the reactor on the shell side. The gas building up in the reactor on the shell side is desirably discharged from the reactor on the shell side to the heating medium discharge pot or to the space above a heating medium pumping device via a piping installed on the circumference of the reactor and a piping inserted to the center. With such degassing pipes, it is made possible to prevent gas from building up in the reactor on the shell side that would cause uneven heat removal in the reactor, thus resulting in an abnormal reaction.

For example, as shown in FIG. 2, it will suffice to install the degassing pipe 14 disposed on the upper part of the shell in the reactor to communicate with the heating medium discharge pot 12 that is located above the upper tube supporting plate of the reactor and discharge the gas through the degassing port 15, or to connect a degassing pipe 25 to a space above the heating medium pumping device 20 thereby to discharge the gas through the nozzle 26.

Figure 3:
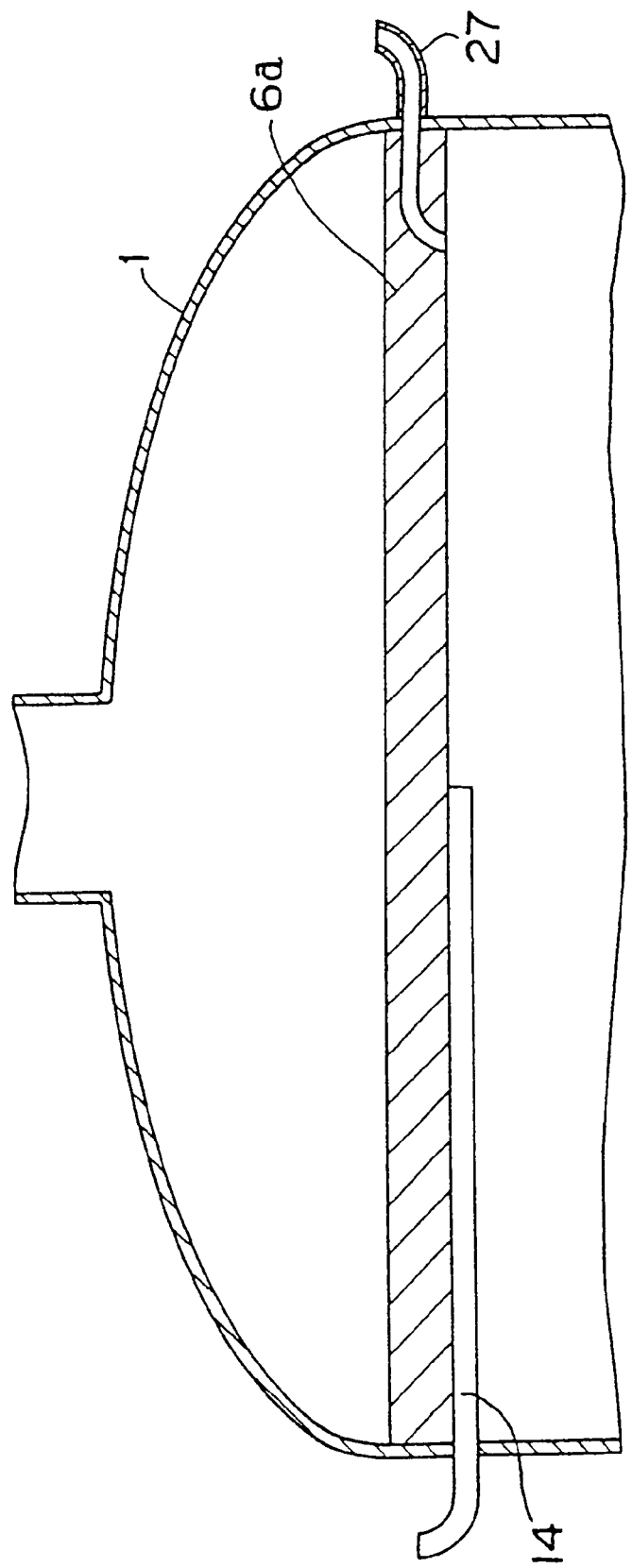
FIG. 3 is a schematic explanatory view showing an example of degassing pipe installation.
Figure 4A:
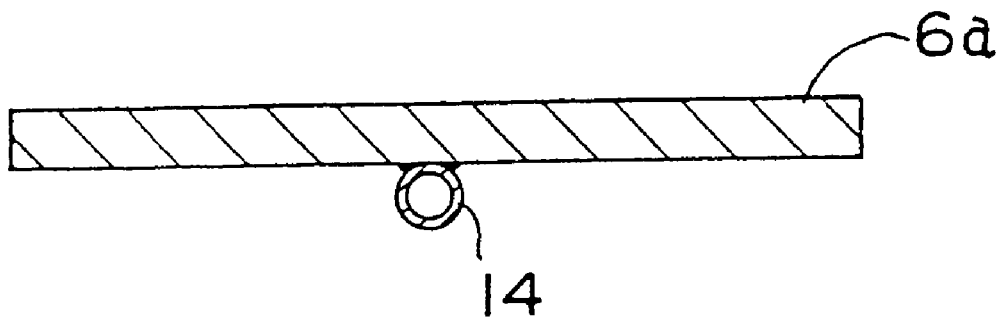
FIGS. 4A and 4B are schematic explanatory views showing examples of degassing pipe configuration.
Figure 4B:
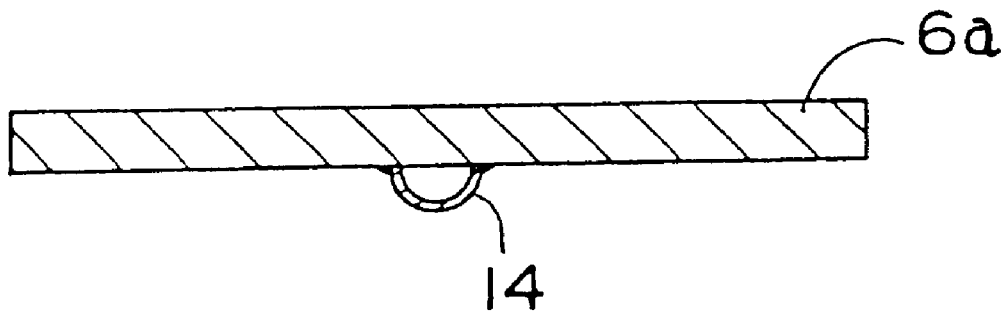

FIG. 3 shows an example of installing the degassing pipe. The gas accumulating along the wall of the reactor may be discharged out of the reactor by forming a flow path in the upper tube supporting plate 6a as indicated by numeral 27, and the gas accumulating at the center of the reactor may be discharged by installing the degassing pipe 14 right below the upper tube supporting plate 6a. The degassing pipe 14 for discharging the gas from the central portion may be a cylindrical pipe having such a cross section as shown in FIG. 4A, or a pipe having semi-circular cross section as shown in FIG. 4B. The semi-circular pipe is preferable for the ease of welding to the upper tube supporting plate 6a and the ease of degassing.

For the heating medium that can be used for the present invention, for example, there are molten salt commonly used as heating medium, and medium based on phenyl-ether such as Dowtherm, but the medium is not limited to these materials.

According to the present invention, as described above, since the heating medium is supplied from the upper part of the shell in the reactor in parallel with the raw material supplied from the top of the reactor, cold heating medium supplied from the upper part of the shell makes contact with a region having the highest exothermal effect in the reactor, in the state of low temperature before heating in the reactor, thus making it possible to achieve high heat exchanging effect and smooth temperature distribution along the axial direction in the reactor.

This makes it possible to suppress hot spot from occurring, achieve smooth temperature distribution in the reactor and easily maintain steady and optimum reacting conditions, thereby achieving highly selective reaction and extending the service life of the oxidation catalyst that fills the tubes, in the catalytic vapor-phase oxidation reaction wherein extremely highly exothermal reaction is performed at a high temperature.

The present invention is further illustrated by the following examples. It is to be understood that the present invention is not limited to the examples, and various design variations made in accordance with the purports described hereinbefore and hereinafter are also included in the technical scope of the present invention.

EXAMPLE 1

In a shell-and-tube reactor comprising ten reaction tubes made of steel having inner diameter of 25.0 mm (outer diameter: 29.0 mm) and length of 4000 mm where a heating medium is circulated on the shell side, the reaction tubes are filled with an oxidation catalyst based on heteropolyacid so that the total length of the catalyst is 2700 mm. A raw material gas consisting of a mixture of methacrolein (5 mol %), oxygen (10 mol %), water vapor (30 mol %) and nitrogen (55 mol %) was supplied from top of the reactor at a space linear velocity of 1500 $Hr^{-1}$ to pass over the catalyst bed, thus performing catalytic vapor-phase oxidation reaction of producing methacrylic acid continuously for 9000 hours. At this time, a heating medium consisting of a molten salt made up of a mixture of potassium nitrate and sodium nitrite (1:1) was supplied from the top of the reactor to flow downward and circulated in parallel with the raw material gas. The catalyst was set to initial temperature of 287° C. and gradually heated at a rate of 1° C. per 1000 hours in order to maintain the conversion ratio of methacrolein constant during the reaction. The results of the reaction are shown in Table 1.

As the Comparative Example, the reaction was performed continuously for 9000 hours under the same conditions as those of Example 1, except that the heating medium was circulated from below the shell side of the reactor upward, that is in the counter-flow direction against the reaction gas. The results of the reaction are shown in Table 1.

TABLE 1

|  | Reaction time (hours) | Heating medium temperature (° C.) | Catalytic layer peak temperature (° C.) | ΔT (° C.) | Methacrolein conversion ratio (%) | Methacrylic acid selectivity (mol %) | Methacrylic acid yield (mol %) |
|---|---|---|---|---|---|---|---|
| Example | 3000 | 290 | 308 | 18 | 91.6 | 81.5 | 74.7 |
|  | 6000 | 293 | 311 | 18 | 91.4 | 81.4 | 74.4 |
|  | 9000 | 296 | 315 | 19 | 91.2 | 81.2 | 74.1 |
| Comp. Example | 3000 | 290 | 313 | 23 | 91.2 | 79.6 | 71.6 |
|  | 6000 | 293 | 317 | 24 | 90.6 | 79.2 | 70.8 |
|  | 9000 | 296 | 320 | 24 | 90.2 | 78.8 | 70.4 |

As shown in Table 1, the reaction of Example 1 was capable of maintaining the peak temperature of the catalyst layer lower than that of the Comparative Example over the reaction period of 9000 hours. As a result, high catalyst performance was maintained over an extended period of time in Example 1, thus achieving high values in all of the methacrolein conversion ratio, methacrylic acid selectivity and methacrylic acid yield.

EXAMPLE 2

In a reactor comprising ten thousand reaction tubes made of steel having inner diameter of 25.0 mm (outer diameter: 29.0 mm) and length of 4000 mm arranged evenly in a cross sectional plane and clamped by upper and lower tube supporting plates, the reaction tubes were filled with an oxidation catalyst based on heteropolyacid so that the total length of the catalyst was 2700 mm. A heating medium consisting of a molten salt made up of a mixture of potassium nitrate and sodium nitrite (1:1) was circulated as shown in FIG. 2.

A raw material consisting of a mixture of methacrolein (5 mol %), oxygen (10 mol %), water vapor (30 mol %) and nitrogen (55 mol %) was supplied from top of the reactor at a space linear velocity of 1500 Hr$^{-1}$ to pass through the catalyst beds in the reaction tubes from above downward, thus performing the reaction of producing methacrylic acid continuously. The catalyst temperature was increased at a rate of 1° C. per 1000 hours in order to maintain the conversion ratio of methacrolein constant during the reaction. The results of the reaction are shown in Table 2, showing that the reaction could be performed in steady state for 20000 hours while keeping the peak temperature of the catalyst layer at a low level comparable to that of Example 1. Also uniform temperature distribution as shown in Table 3 was observed in the direction of cross section in the upper zone of the reactor during the reaction, and no abnormality in heat removal that accompanies gas build-up inside the reactor on the shell side was observed.

TABLE 2

| Reaction time (hours) | Heating medium temperature (° C.) | Catalytic layer peak temperature (° C.) | ΔT (° C.) | Methacrolein conversion ratio (%) | Methacrylic acid selectivity (mol %) | Methacrylic acid yield (mol %) |
|---|---|---|---|---|---|---|
| 3000 | 290 | 308 | 18 | 91.4 | 81.3 | 74.3 |
| 20000 | 307 | 326 | 19 | 91.0 | 81.0 | 73.7 |

TABLE 3

| Reaction time | Distance from reactor wall | | |
|---|---|---|---|
| (hours) | 500 mm | 1000 mm | 1800 mm |
| 3000 | 290.5° C. | 290.5° C. | 290.7° C. |
| 20000 | 307.4° C. | 307.6° C. | 307.6° C. |

EXAMPLE 3

In a shell-and-tube reactor comprising ten reaction tubes made of steel having inner diameter of 25.0 mm (outer diameter: 29.0 mm) and length of 3000 mm where a heating medium is circulated on the shell side, the reaction tubes were filled with a vanadium-titanium-based oxidation catalyst so that the total length of the catalyst is 2500 mm. A raw material gas consisting of a mixture gas of oxygen (10 mol %), water vapor (10 mol %) and nitrogen (80 mol %) mixed with naphthalene in a proportion of 85 g/Nm$^3$ was supplied from top of the reactor at a space linear velocity of 2500 Hr$^{-1}$ to pass over the catalyst bed, thus performing catalytic vapor-phase oxidation reaction of producing phthalic anhydride continuously for 6000 hours. At this time, a heating medium consisting of a molten salt made up of a mixture of potassium nitrate and sodium nitrite (1:1) was supplied from the top of the reactor to the shell side and circulated in parallel with the reaction gas. The temperature of the heating medium was maintained constant at 340° C. The results of the reaction are shown in Table 4.

As the Comparative Example, the reaction was performed continuously for 6000 hours under the same conditions as those of Example 3, except that the heating medium was circulated from below the shell side of the reactor upward, that is in the counter-flow direction against the reaction gas. The results of the reaction are shown in Table 4.

TABLE 4

| | Reaction time (hours) | Heating medium temperature (° C.) | Catalytic layer peak temperature (° C.) | ΔT (° C.) | Phthalic anhydride yield (mol %) |
|---|---|---|---|---|---|
| Example 3 | 3000 | 340 | 385 | 42 | 91.0 |
| | 6000 | 340 | 385 | 43 | 90.8 |
| Comp. Example 3 | 3000 | 340 | 390 | 50 | 89.9 |
| | 6000 | 340 | 391 | 51 | 89.6 |

As shown in Table 4, the reaction of Example 3 was capable of maintaining the peak temperature of the catalyst layer lower than that of Comparative Example 3 over the reaction period of 6000 hours. As a result, high catalyst performance was maintained over an extended period of time in Example 3, while achieving high yield of phthalic anhydride. In Comparative Example 3, achieving a level of yield comparable to that of Example 3 would require it to further increase the reaction temperature, that would accelerate the deterioration of the catalyst.

The present invention, with such a construction as described above, provides the catalytic vapor-phase oxidation reaction capable of suppressing the occurrence of hot spot, and the shell-and-tube reactor that can be preferably used in the method.

Having thus described and exemplified the present invention with a certain degree of particularity, it should be appreciated that the following claims are not to be so limited but are to be afforded a scope commensurate with the wording of each element of the claim and equivalents thereof.

What is claimed is:

1. A shell-and-tube reactor comprising:
   a chamber including:
      a gas inlet in an upper part of the chamber;
      a gas outlet in a lower part of the chamber;
      a shell between the gas inlet and the gas outlet, the shell being defined by an upper tube supporting plate, a lower tube supporting plate and a side wall of the chamber;
   a plurality of reaction tubes supported by the upper and lower tube supporting plates for introducing material gas from the gas inlet and discharging a reaction product to the gas outlet;
   a heating medium supplying system for supplying a liquid heating medium in the shell, the heating medium supplying system including:
      a heating medium introducing port provided on an upper part of the shell;
      a heating medium discharge port provided on a lower part of the shell; and
      a back pressure applier for imparting a back pressure to the heating medium in the shell so that a top of the liquid heating medium in the shell comes into contact with a lower surface of the upper tube supporting plate; and
      wherein the back pressure applier comprises a heating medium discharge pot arranged above the upper tube supporting plate.

2. A shell-and-tube reactor according to claim 1 further comprising a gas discharging means disposed on a top part of the shell for degassing a gas from the shell to an outside of the reactor.

3. A shell-and-tube reactor according to claim 2, wherein the gas discharging means includes a degassing pipe disposed at a lower surface of the upper tube supporting plate.

4. A shell-and-tube reactor according to claim 3, wherein the degassing pipe extends to around a center of the upper tube supporting plate.

5. A shell-and-tube reactor according to claim 2, wherein the gas discharging means includes a gas flow path formed in the upper tube supporting plate.

6. A shell-and-tube reactor according to claim 1, further comprising a degassing port disposed on an upper part of the heating medium discharge pot, the reactor further comprising a gas discharging means disposed on a top part of the shell and connected to the discharge port for degassing a gas from the shell to an outside of the reactor.

7. A shell-and-tube reactor according to claim 1, wherein the shell includes one or more baffle plates for changing a flow direction of the heating medium.

8. A shell-and-tube reactor according to claim 1, wherein the heating medium supplying system further comprises a heating medium pumping device provided between the heating medium introducing port and the heating medium discharge port.

9. A shell-and-tube reactor according to claim 8, further comprising a gas discharging means disposed on a top part of the shell and connected to the heating medium pumping device for degassing through a degassing port disposed on an upper part of the heating medium pumping device.

10. A shell-and-tube reactor according to claim 1, wherein the back pressure applier comprises an orifice.

11. A shell-and-tube reactor comprising:
    a chamber including:
       a gas inlet in an upper part of the chamber;
       a gas outlet in a lower part of the chamber;
       a shell between the gas inlet and the gas outlet, the shell being defined by an upper tube supporting plate, a lower tube supporting plate and a side wall of the chamber;
    a plurality of reaction tubes supported by the upper and lower tube supporting plates for introducing material gas from the gas inlet to the gas outlet through the shell;
    a heating medium supplying system for supplying a liquid heating medium in the shell, the heating medium supplying system including:
       a heating medium introducing port provided on an upper part of the shell;
       a heating medium discharge port provided on a lower part of the shell;
       a back pressure applier for imparting a back pressure to the heating medium in the shell so that a top of the liquid heating medium in the shell comes into contact with a lower surface of the upper tube supporting plate;
       wherein the back pressure applier comprises a heating medium discharge pot arranged above the upper tube supporting plate; and
       a gas discharging means for discharging a gas from a top of the shell to an outside of the reactor so that a top of the liquid heating medium in the shell comes into contact with a lower surface of the upper tube supporting plate.

12. A shell-and-tube reactor according to claim 11, wherein the gas discharging means includes a degassing pipe disposed at a lower surface of the upper tube supporting plate.

13. A shell-and-tube reactor according to claim 11, wherein the gas discharging means includes a gas flow path formed in the upper tube supporting plate.

* * * * *